(12) United States Patent
Glasmachers et al.

(10) Patent No.: US 10,161,867 B2
(45) Date of Patent: Dec. 25, 2018

(54) METHOD AND MEASURING DEVICE FOR DETERMINING A PROPERTY OF A MEDIUM

(71) Applicant: KROHNE Messtechnik GmbH, Duisburg (DE)

(72) Inventors: Holger Glasmachers, Bochum (DE); Edin Andelic, Hagen (DE); Andreas Schwaner, Alpen (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 0 days.

(21) Appl. No.: 15/800,228

(22) Filed: Nov. 1, 2017

(65) Prior Publication Data

US 2018/0120226 A1 May 3, 2018

(30) Foreign Application Priority Data

Nov. 1, 2016 (DE) .................. 10 2016 120 785

(51) Int. Cl.
| | | |
|---|---|---|
| G01N 21/00 | (2006.01) | |
| G01N 21/49 | (2006.01) | |
| G01N 27/04 | (2006.01) | |
| G01N 27/02 | (2006.01) | |
| G01N 21/53 | (2006.01) | |

(52) U.S. Cl.
CPC .......... *G01N 21/49* (2013.01); *G01N 27/028* (2013.01); *G01N 27/04* (2013.01); *G01N 21/534* (2013.01)

(58) Field of Classification Search
CPC ............... G01N 21/53; G01N 15/0205; G01N 15/1459; G01N 21/51; G01N 15/1434

USPC ......................................................... 356/338
See application file for complete search history.

(56) References Cited

U.S. PATENT DOCUMENTS

| 2003/0090269 | A1* | 5/2003 | Fanini | ...................... G01V 3/28 324/339 |
|---|---|---|---|---|
| 2004/0001267 | A1* | 1/2004 | Chliwnyj | ............... G11B 5/584 360/31 |
| 2012/0162645 | A1* | 6/2012 | Andelic | ................. G01N 21/49 356/338 |
| 2013/0024150 | A1* | 1/2013 | Erb | ........................ G01R 23/16 702/76 |
| 2016/0041236 | A1* | 2/2016 | Nakayama | ......... G01R 33/0029 324/239 |

* cited by examiner

*Primary Examiner* — Md M Rahman
(74) *Attorney, Agent, or Firm* — David S. Safran; Roberts Mlotkowski Safran Cole & Calderon, P.C.

(57) ABSTRACT

A method for determining a property of a medium, wherein an excitation signal is generated and transmitted into the medium, a measuring signal is generated from the excitation signal transmitted into the medium, the measuring signal is measured, an amplitude of the excitation signal and an amplitude of the measuring signal are determined, and the property of the medium is determined using the amplitude of the excitation signal and the amplitude of the measuring signal. To provide a method in which the accuracy of determination of the property of the medium is improved, the amplitude of the excitation signal is determined by digitizing the excitation signal and applying a lock-in method to the digitized excitation signal and determining the amplitude of the measuring signal by digitizing the measuring signal and applying the lock-in method to the digitized measuring signal.

10 Claims, 3 Drawing Sheets

METHOD AND MEASURING DEVICE FOR DETERMINING A PROPERTY OF A MEDIUM

BACKGROUND OF THE INVENTION

Field of the Invention

The invention relates, on the one hand, to a method for determining a property of a medium. In this method, an excitation signal is first generated and transmitted into the medium. A measuring signal is generated by the excitation signal transmitted into the medium and is then measured. Furthermore, an amplitude of the excitation signal and an amplitude of the measured measuring signal are determined and the property of the medium is determined using the amplitude of the excitation signal and the amplitude of the measuring signal.

On the other hand, the invention also relates to a measuring device for determining a property of a medium. The measuring device has an excitation unit, a measuring unit and a control unit, wherein the control unit is designed for controlling both the excitation unit and the measuring unit. During operation of the measuring device, the excitation unit first generates an excitation signal and transmits the excitation signal into the medium. The excitation signal transmitted into the medium generates a measuring signal in the measuring unit, wherein the measuring unit then measures the measuring signal. Further, the control unit determines an amplitude of the excitation signal and an amplitude of the measured measuring signal and determines the property of the medium using the amplitude of the excitation signal and the amplitude of the measuring signal.

Description of Related Art

Inductive conductivity measuring devices and turbidity measuring devices are known from the prior art as measuring devices of the type described, which, during operation, also carry out methods of the type described.

Such an inductive conductivity measuring device measures the electrical conductivity of the medium as the property of the medium. The excitation unit of an inductive conductivity measuring device usually has an excitation coil for transmitting the excitation signal into the medium and the measuring unit has a measuring coil for measuring the measuring signal. The control unit, for example, for determining the amplitude of the excitation signal and the amplitude of the measuring signal, has, in each case, an analog lock-in amplifier. In general, a lock-in amplifier is an amplifier for measuring a weak alternating signal. In order to measure the alternating signal, the lock-in amplifier modulates the alternating signal with a reference alternating signal having a known reference frequency and acts as a narrow bandpass filter, which means that direct signals, alternating signals having frequencies deviating from the reference frequency, and noise in the alternating signal to be measured are reduced. In this manner, the signal-to-noise ratio of the alternating signal is improved. A lock-in amplifier usually has a signal input for the alternating signal to be measured, a reference signal source for generating the reference alternating signal, a phase shifter, a mixer and a low-pass filter. The phase shifter causes the alternating signal modulated with the reference alternating signal and the reference alternating signal to be in phase. The multiplier then mixes the alternating signal and the reference alternating signal together, and the low-pass filter filters the result of the mixing. The low-pass-filtered result is proportional to the amplitude of the unmodulated alternating signal.

The excitation unit of a turbidity measuring device of the type described usually has a light source for transmitting the excitation signal into the medium and the measuring unit has a light sensor for measuring the measuring signal. The control unit of a turbidity measuring device also has, for example, an analog lock-in amplifier, in each case, for determining the amplitude of the excitation signal and the amplitude of the measuring signal. In this respect, the explanations in respect to the inductive conductivity measuring device apply accordingly to the turbidity measuring device.

SUMMARY OF THE INVENTION

The object of the present invention is to provide a method and a measuring device for determining a property of a medium in which the accuracy of the determination of the property of the medium is improved.

According to a first teaching, the invention relates to a method for determining a property of a medium in which the indicated task is achieved. The method according to the invention is initially and essentially wherein the amplitude of the excitation signal is determined by digitizing the excitation signal and applying a lock-in method to the digitized excitation signal. Further, it is wherein the amplitude of the measuring signal is determined by digitizing the measurement signal and applying the lock-in method to the digitized measuring signal.

In methods known from the prior art, the determination of the amplitude of the excitation signal and the determination of the amplitude of the measuring signal are carried out by the execution of lock-in methods in the analog domain. The analog domain is wherein analog signals are processed analogously. Processing means, for example, e.g. to amplify, to filter or to mix. Generally, in the case of a lock-in method, as in the case of a lock-in amplifier, for measuring a alternating signal, this is first modulated with a reference alternating signal having a known reference frequency. Then the modulated alternating signal and the reference alternating signal are brought into phase and the two signals are then mixed with one another. Finally, the result of the mixing is low-pass filtered. The low-pass-filtered result of the mixing is proportional to the amplitude of the unmodulated alternating signal. In the case of a digital lock-in method, the excitation signal and the measuring signal are first digitized before the lock-in method is carried out and the lock-in method follows in the digital domain. The digital domain is wherein digital signals are digitally processed. Processing means, for example, e.g. to amplify, to filter or to mix. Carrying out the lock-in method in the digital domain rather than in the analog domain improves the accuracy of the determination of the property of the medium compared to execution in the analog domain. Because of this, the requirements for the units carrying out the methods are reduced, whereby production costs are also reduced.

In an implementation of the method according to the invention, it is provided that a Goertzel algorithm is performed when the digital lock-in method is carried out. This implementation is based on the recognition that a lock-in method corresponds to a bandpass filter and can be performed by a Goertzel algorithm and subsequent low-pass filtering.

In a further implementation of the method, it is provided that a signal plausibility check is carried out using the digitized excitation signal and the digitized measuring signal. Preferably, a SIL2 signal plausibility check is carried out. SIL stands for the expression Safety Integrity Level, which is known from the international standard IEC 61508/IEC61511.

According to a second teaching, the invention relates to a measuring device for determining a property of a medium in which the indicated task is achieved. The measuring device according to the invention is initially and essentially wherein the control unit determines the amplitude of the excitation signal by digitizing the excitation signal and carrying out a lock-in method on the digitized excitation signal. Furthermore, the measuring device is wherein the control unit determines the amplitude of the measuring signal by digitizing the measuring signal and carrying out the lock-in method on the digitized medium. Both are carried out by the control unit during operation of the measuring device.

Measuring devices of the present type known from the prior art have analog lock-in amplifiers. It has been recognized that these lock-in amplifiers cause errors in the determination of the property of the medium due to their analog signal processing and a considerable analog circuitry is necessary to reduce these errors. In contrast, the determination of the property of the medium according to the invention takes place only after the digitization of both the excitation signal and the measuring signal and thus in the digital domain, thereby avoiding these errors. Thus, the analog lock-in amplifiers can be dispensed with, thereby reducing the manufacturing costs and improving the accuracy of the determination of the property of the medium.

In one design of the measuring device according to the invention, it is provided that the control unit is designed for carrying out one of the described methods.

In a further design of the measuring device, it is provided that the measuring device is an inductive conductivity measuring device. The excitation unit has an excitation coil for transmitting the excitation signal into the medium and the measuring unit has a measuring coil for measuring the measuring signal. The measuring device determines electrical conductivity as the property of the medium using the ratio of the amplitude of the measuring signal to the amplitude of the excitation signal. The excitation signal is thereby transmitted as eddy current through the medium from the excitation coil to the measuring coil.

A ratio of the amplitude of the measuring signal to the amplitude of the excitation signal is a measure of the conductivity of the medium. The transmission of the excitation signal from the excitation coil to the measurement coil takes place, on the one hand, with the medium and, on the other hand, with a magnetic residual coupling, which is independent of the medium, between the measuring coil and the excitation coil. This medium-independent residual coupling causes an error in the determination of the electrical conductivity of the medium, which is why this error must be compensated.

Two methods for compensating the error are known from the prior art. Both methods have in common that, in a first method step, a measuring signal generated by the residual coupling is determined. This is done by transmitting the excitation signal from the excitation coil to the measuring coil in the absence of a medium, whereby it is ensured that the transmission of the excitation signal is not effected by the medium. Thus, the measuring signal generated in this manner corresponds to the error by the medium-independent residual coupling. According to the first known method, the measuring signal caused by the residual coupling is subtracted from the measuring signal, which is determined in the presence of a medium. According to the second known method, the effect of the residual coupling is compensated by a compensating winding with an adjustable resistance. In this case, the resistance value of the adjustable resistance is varied until no measured signal is measured during the measurements without the medium. Both methods therefore also have in common that compensation takes place after the respective measurement and thus after the execution of a lock-in method. It has been recognized that this retrospective compensation leads to errors. Therefore, in a further development of the above design, it is provided that the control unit compensates for a medium-independent residual coupling between the excitation coil and the measuring coil before the lock-in method is carried out.

In an alternative design of the measuring device, it is provided that it is not an inductive conductivity measuring device, but a turbidity measuring device. In this case, the excitation unit has a light source for transmitting the excitation signal into the medium and the measuring unit has a light sensor for measuring the measuring signal. The measuring device determines turbidity as the property of the medium using the ratio of the amplitude of the measuring signal to the amplitude of the excitation signal. In this case, the excitation signal is transmitted as light generated by the light source via the medium.

In one design of the turbidity measuring device, it is provided that the excitation unit has a further light sensor for measuring the excitation signal.

In a further design of the turbidity measuring device, it is provided that the light source, the medium and the light sensor are arranged in such a manner that the excitation signal generated by the light source and transmitted by the medium directly strikes the light sensor. Thereby, the light in the medium is scattered on components of the medium that turbidify the medium, so that the light transmitted from the medium to the light sensor is a measure of the turbidity of the medium.

In a design alternative to the above design of the turbidity measuring device, the light source, the medium and the light sensor are arranged in such a manner that the excitation signal generated by the light source is scattered by the medium and the scattered excitation signal strikes the light sensor. Thereby, the light in the medium is scattered on components of the medium that turbidify the medium, so that the scattered light transmitted from the medium to the light sensor is a measure of the turbidity of the medium.

The explanations in respect to the first teaching of the invention also apply accordingly to the second teaching of the invention and vice versa.

In detail, there is a plurality of possibilities for designing and further developing the method and measuring device according to the invention for determining a property of the medium as will be apparent from the following description of preferred embodiments in conjunction with the accompanying drawings.

DETAILED DESCRIPTION OF THE INVENTION

Figure 1:
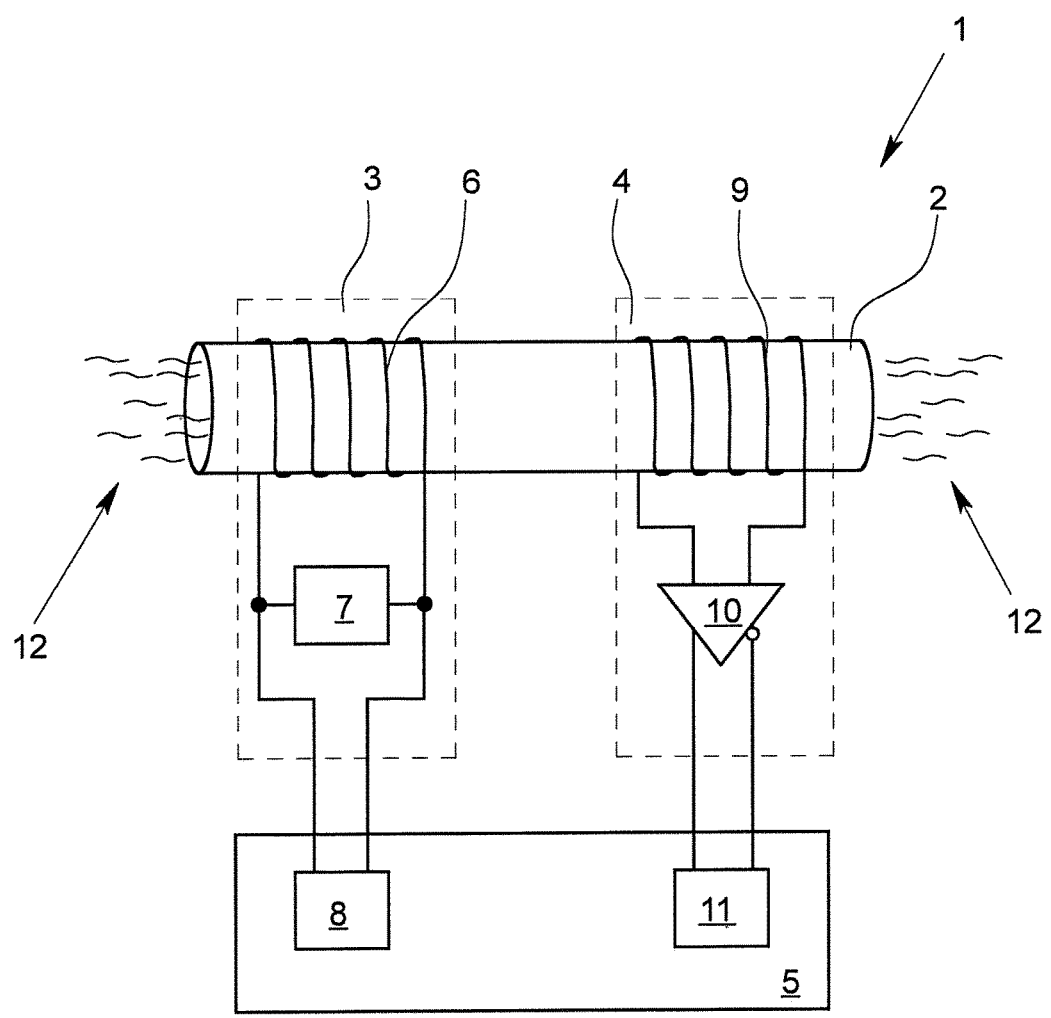
FIG. 1 shows a first embodiment of a measuring device for determining a property of a medium.

FIG. 1 shows a first embodiment of a measuring device 1, wherein the measuring device is an inductive conductivity measuring device. The measuring device has a measuring tube 2, an excitation unit 3, a measuring unit 4 and a control unit 5. The excitation unit 3 has an excitation coil 6 and an excitation source 7, wherein a first analog-to-digital converter 8 belongs to the control unit 5. The measuring unit 4 has a measuring coil 9 and an amplifier 10, wherein a second analog-to-digital converter 11 belongs to the control unit 5.

During operation of the measuring device 1, a medium 12 is in the measuring tube 2, and electrical conductivity is determined as a property of the medium 12 by the measuring device 1. For this, the excitation unit 3 generates an excitation signal with the excitation source 7 and transmits it into the medium 12 with the excitation coil 6. The excitation signal transmitted into the medium 12 generates a measuring signal by induction in the measuring coil 9 of the measuring unit 4, which is measured by the measuring unit 4 and amplified with the amplifier 10. The transmission of the excitation signal from the excitation coil 6 to the measuring coil 9 takes place by means of eddy currents in the medium 12.

Both the excitation signal and the amplified measuring signal are supplied to the control unit 5. The control unit 5 first determines an amplitude of the supplied excitation signal and an amplitude of the supplied measuring signal. For this, the control unit 5 digitizes the excitation signal with the first analog-to-digital converter 8 and the measuring signal with the second analog-to-digital converter 11. The amplification of the measuring signal by the amplifier 10 is set such that an input signal range of the second analog-to-digital converter 11 is exploited. Further, the control unit 5 determines the amplitude of the excitation signal by carrying out a lock-in method on the digitized excitation signal and, by carrying out the lock-in method on the digitized measuring signal, determines the amplitude of the measuring signal. In carrying out the lock-in method, the control unit 5 also performs a Goertzel algorithm. Using the ratio of the amplitude of the measuring signal to the amplitude of the excitation signal, the conductivity of the medium 12 is then determined.

Further, the control unit 5 carries out a SIL2 signal plausibility check using the digitized excitation signal and the digitized measurement signal. In addition, the control unit 5 compensates for a medium-independent residual coupling between the excitation coil and the measuring coil before the execution of the lock-in method.

Figure 2:
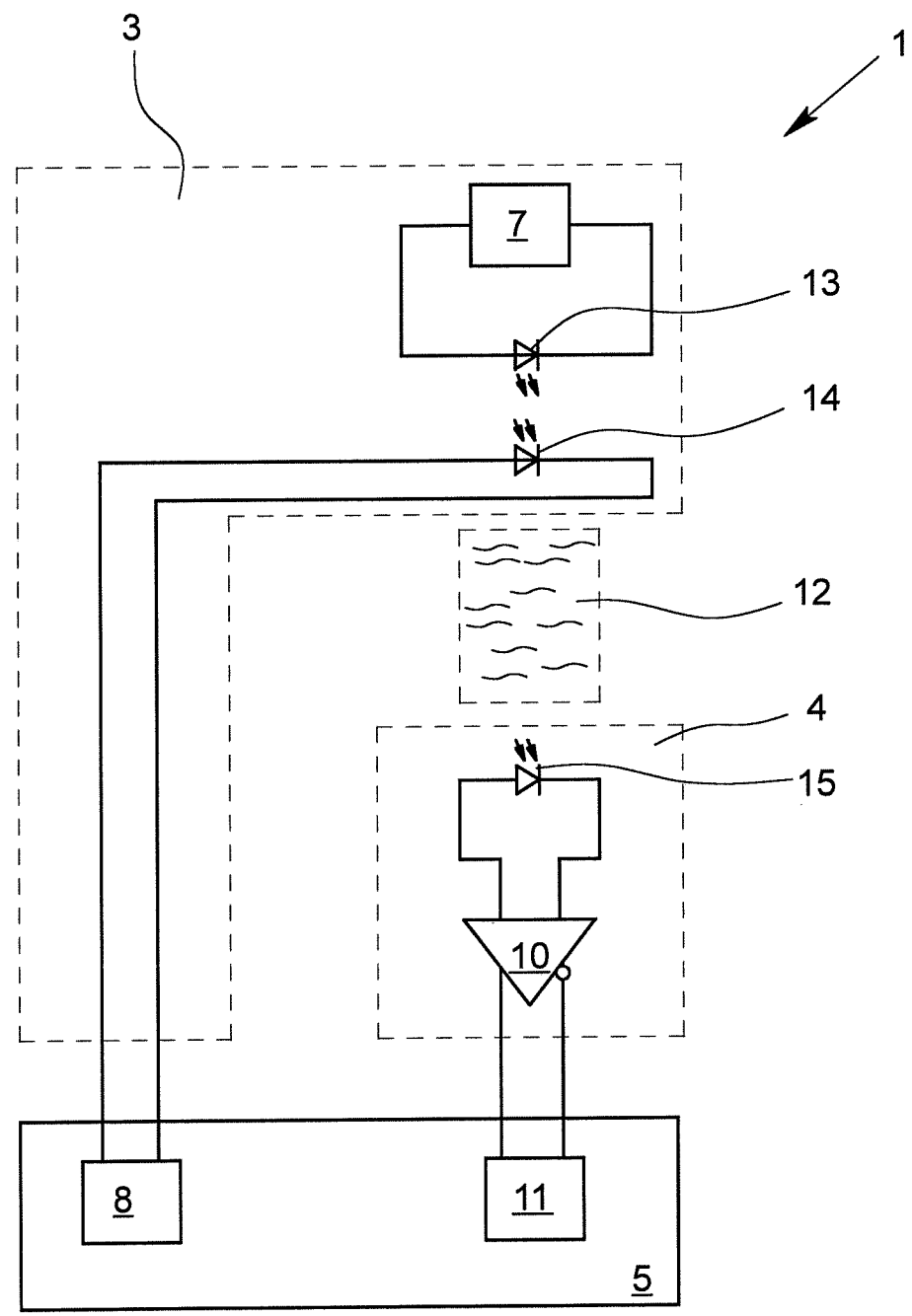
FIG. 2 shows a second embodiment of such a measuring device.

FIG. 2 shows a second embodiment of a measuring device, which is a first turbidity measuring device. The measuring device 1 has an excitation unit 3, a measuring unit 4 and a control unit 5. The excitation unit 3 has a light source 13, an excitation source 7 and an excitation light sensor 14. The measuring device 4 has a light sensor 15 and an amplifier 10. The control unit 5 has a first analog-to-digital converter 8 and a second analog-to-digital converter 11.

During operation of the measuring device 1, turbidity is determined as a property of a medium 12 by the measuring device 1. For this, the excitation unit 3 generates an excitation signal with the excitation source 7 and transmits the excitation signal into the medium 12 using the light source 13. The excitation signal transmitted into the medium 12 generates a measurement signal in the light sensor 15, which is measured by the measuring unit 4 and is amplified with the amplifier 10. The transmission of the excitation signal from the light source 13 to the light sensor 15 is effected by light in the medium 12. The light source 13, the medium 12 and the light sensor 15 are arranged in such a manner that the excitation signal generated by the light source 13 and transmitted by the medium 12 directly strikes the light sensor 15. The light is scattered in the medium 12 on the components 12 of the medium 12 that turbidify the medium 12 so that the light transmitted from the medium 12 to the light sensor 15 is a measure of the turbidity of the medium 12. The excitation signal is measured by the excitation unit 3 with the excitation light sensor 14.

Both the measured excitation signal and the amplified, measured measuring signal are supplied to the control unit 5. The control unit 5 first determines an amplitude of the supplied excitation signal and an amplitude of the supplied measuring signal. For this, the control unit 5 digitizes the excitation signal with the first analog-to-digital converter 8 and the measuring signal with the second analog-to-digital converter 11. The amplification of the measuring signal by the amplifier 10 is set such that an input signal range of the second analog-to-digital converter 11 is exploited. Further, the control unit 5 determines the amplitude of the excitation signal by carrying out a lock-in method on the digitized excitation signal and, by executing the lock-in method on the digitized measuring signal, determines the amplitude of the measuring signal. In carrying out the lock-in method, the control unit 5 also performs a Goertzel algorithm. Using the ratio of the amplitude of the measuring signal to the amplitude of the excitation signal, the turbidity of the medium 12 is then determined. Further, the control unit 5 performs a SIL2 signal plausibility check using the digitized excitation signal and the digitized measurement signal.

Figure 3:
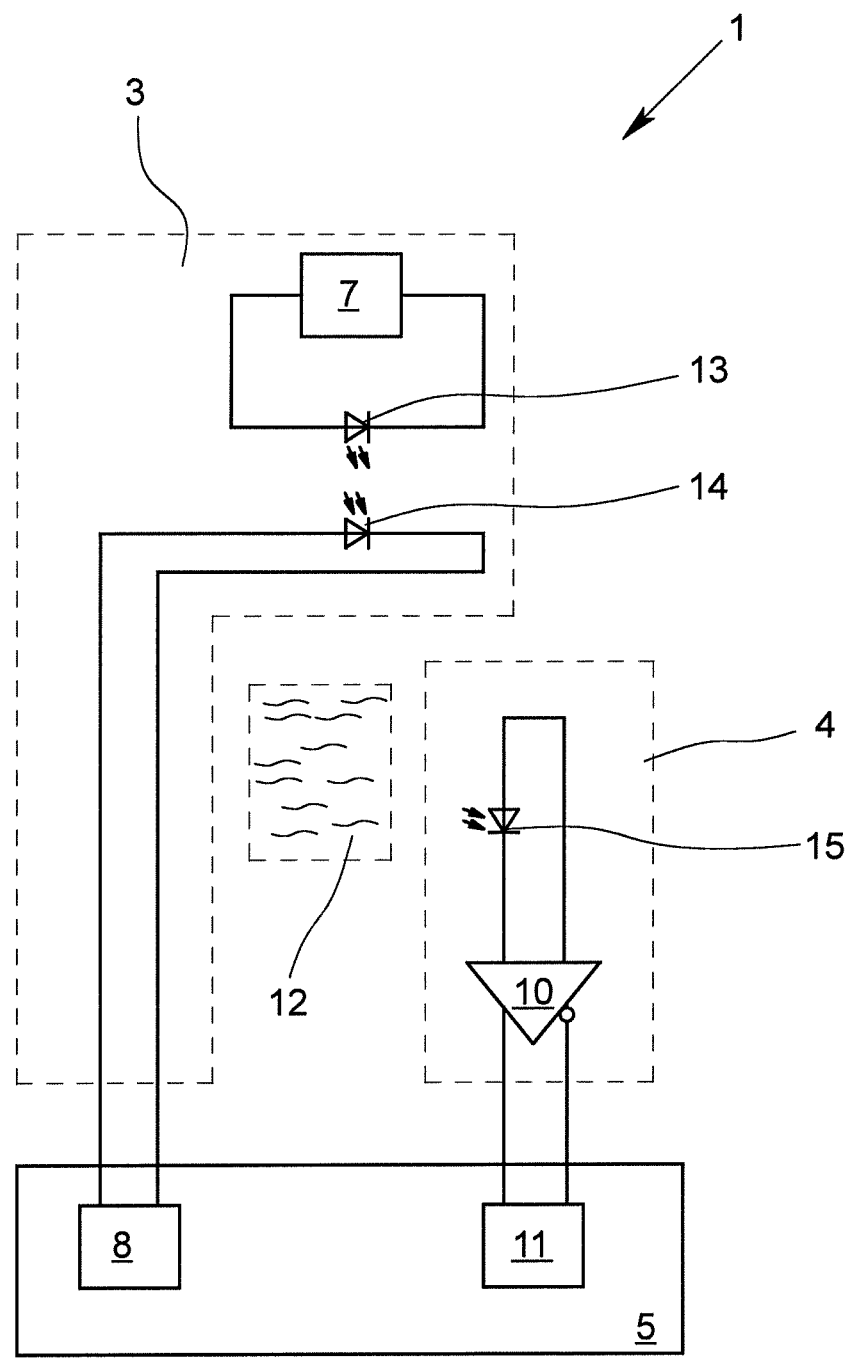
FIG. 3 shows a third embodiment of such measuring device.

FIG. 3 shows a third embodiment of a measuring device, which is a second turbidity measuring device. The measuring device 1 has an excitation unit 3, a measuring unit 4 and a control unit 5. The excitation unit 3 has a light source 13, an excitation source 7 and an excitation light sensor 14. The measuring unit 4 has a light sensor 15 and an amplifier 10. The control unit 5 has a first analog-to-digital converter 8 and a second analog-to-digital converter 11.

During operation of the measuring device 1, turbidity is determined as a property of a medium 12 by the measuring device 1. For this, the excitation unit 3 generates an excitation signal with the excitation source 7 and transmits the excitation signal into the medium 12 using the light source 13. The excitation signal transmitted to the medium 12 generates a measuring signal in the light sensor 15 which is measured by the measuring unit 4 and is amplified with the amplifier 10. The transmission of the excitation signal from the light source 13 to the light sensor 15 is effected by light in the medium 12. The light source 13, the medium 12 and the light sensor 15 are arranged relative to one another in such a manner that the excitation signal generated by the light source 13 indirectly strikes the light sensor 15. The light is thereby scattered in the medium 12 on the components 12 of the medium 12 that turbidify the medium 12, and the scattered light then strikes the light sensor 15, wherein the scattered light is a measure of the turbidity of the medium 12. The excitation signal is measured by the excitation unit 3 with the excitation light sensor 14.

Both the measured excitation signal and the amplified, measured measuring signal are supplied to the control unit 5. The control unit 5 first determines an amplitude of the supplied excitation signal and an amplitude of the supplied measuring signal. For this, the control unit 5 digitizes the excitation signal with the first analog-to-digital converter 8 and the measuring signal with the second analog-to-digital converter 11. The amplification of the measuring signal by the amplifier 10 is set such that an input signal range of the second analog-to-digital converter 11 is exploited. Further, the control unit 5 determines the amplitude of the excitation signal by carrying out a lock-in method on the digitized excitation signal and, by carrying out the lock-in method on the digitized measuring signal, determines the amplitude of the measuring signal. Using the ratio of the amplitude of the measuring signal to the amplitude of the excitation signal, the turbidity of the medium 12 is then determined.

What is claimed is:

1. A method for determining a property of a medium, comprising:
   generating an excitation signal,
   transmitted the generated excitation signal into the medium,
   generating a measuring signal from the excitation signal transmitted into the medium,
   measuring the measuring signal generated,
   determining an amplitude of the excitation signal and an amplitude of the measuring signal, and
   determining the property of the medium using the amplitude of the excitation signal and the amplitude of the measuring signal determined,
   wherein the amplitude of the excitation signal is determined by digitizing the excitation signal and applying a lock-in method to the digitized excitation signal and
   wherein the amplitude of the measuring signal is determined by digitizing the measuring signal and applying the lock-in method to the digitized measuring signal.

2. The method according to claim 1, wherein a Goertzel algorithm is performed when the lock-in method is carried out.

3. The method according to claim 1, wherein a signal plausibility check is performed using the digitized excitation signal and the digitized measuring signal.

4. A measuring device for determining a property of a medium, comprising:
   an excitation unit having means for generating an excitation signal and transmitting the excitation signal into the medium so as to generate a measuring signal,
   a measuring unit having means for measuring the measuring signal and
   a control unit having means for determining an amplitude of the excitation signal and an amplitude of the measuring signal and for determining the property of the medium using the amplitude of the excitation signal and the amplitude of the measuring signal,
   wherein the control unit has means for determining the amplitude of the excitation signal by digitizing the excitation signal and carrying out a lock-in method on the digitized excitation signal and
   wherein the control unit has means for determining the amplitude of the measuring signal by digitizing the measuring signal and carrying out the lock-in method on the digitized measuring signal.

5. The measuring device according to claim 4, wherein the measuring device is an inductive conductivity measuring device, the excitation unit has an excitation coil for transmitting the excitation signal into the medium, the measuring unit has a measuring coil for measuring the measuring signal, and the property of the medium determined is an electrical conductivity property of the medium.

6. The measuring device according to claim 5, wherein the control unit has means for compensating for a medium-independent residual coupling between the excitation coil and the measuring coil before the lock-in method is carried out.

7. The measuring device according to claim 4, wherein the measuring device is a turbidity measuring device, the excitation unit has a light source for transmitting the excitation signal into the medium, the measuring unit has a light sensor for measuring the measuring signal, and the property of the medium determined is a turbidity property of the medium.

8. The measuring device according to claim 7, wherein the excitation unit has an excitation light sensor for measuring the excitation signal.

9. The measuring device according to claim 7, wherein the light source, the medium and the light sensor are arranged such that the excitation signal generated by the light source and transmitted by the medium directly strikes the light sensor.

10. The measuring device according to claim 7, wherein the light source, the medium and the light sensor are arranged such that the excitation signal generated by the light source is scattered by the medium and the scattered excitation signal strikes the light sensor.

* * * * *